United States Patent [19]
Waschke et al.

[11] Patent Number: 4,875,477
[45] Date of Patent: Oct. 24, 1989

[54] PROTECTIVE MASK HAVING A BUILT-IN SENSOR FOR MONITORING VITAL FUNCTIONS

[75] Inventors: Christine Waschke, Lübeck; Lothar Töpfer, Ratingen; Alfred Rath, Hamberge, all of Fed. Rep. of Germany

[73] Assignee: Drägerwerk Aktiengesellschaft, Lübeck, Fed. Rep. of Germany

[21] Appl. No.: 211,966

[22] Filed: Jun. 27, 1988

[30] Foreign Application Priority Data
Jul. 23, 1987 [DE] Fed. Rep. of Germany ....... 3724336

[51] Int. Cl.⁴ ...................... A62B 18/02; A62B 18/08; A61B 5/02
[52] U.S. Cl. .............................. 128/206.21; 128/670; 128/206.24; 128/206.26
[58] Field of Search .................... 128/206.21, 206.26, 128/206.24, 714, 736, 691, 687, 672, 670

[56] References Cited

U.S. PATENT DOCUMENTS

| | | | |
|---|---|---|---|
| 3,330,274 | 7/1967 | Bennett | 128/206.26 |
| 3,658,054 | 4/1972 | Iberall | 128/672 |
| 4,090,504 | 5/1978 | Nathan | 128/670 |
| 4,230,125 | 10/1980 | Schneider | 128/670 |
| 4,301,808 | 11/1981 | Taus | 128/687 |
| 4,407,295 | 10/1983 | Steuer et al. | 128/670 |

FOREIGN PATENT DOCUMENTS

| | | | |
|---|---|---|---|
| 3106315 | 9/1982 | Fed. Rep. of Germany | |
| 428338 | 5/1934 | United Kingdom | 128/206.24 |
| 2074457 | 11/1981 | United Kingdom | 128/206.21 |

Primary Examiner—Edgar S. Burr
Assistant Examiner—Kimberly L. Asher
Attorney, Agent, or Firm—Walter Ottesen

[57] ABSTRACT

An arrangement for monitoring vital functions includes at least one sensor held against the body. The arrangement of the invention provides a simple and reliable positioning of the sensor even under difficult conditions of use especially with breathing protection equipment. The arrangement according to the invention requires no additional holding devices exclusively for the purpose of mounting the sensor which could possibly be disturbing to the wearer. The sensor is mounted on the inner side of the breathing protective mask.

4 Claims, 1 Drawing Sheet

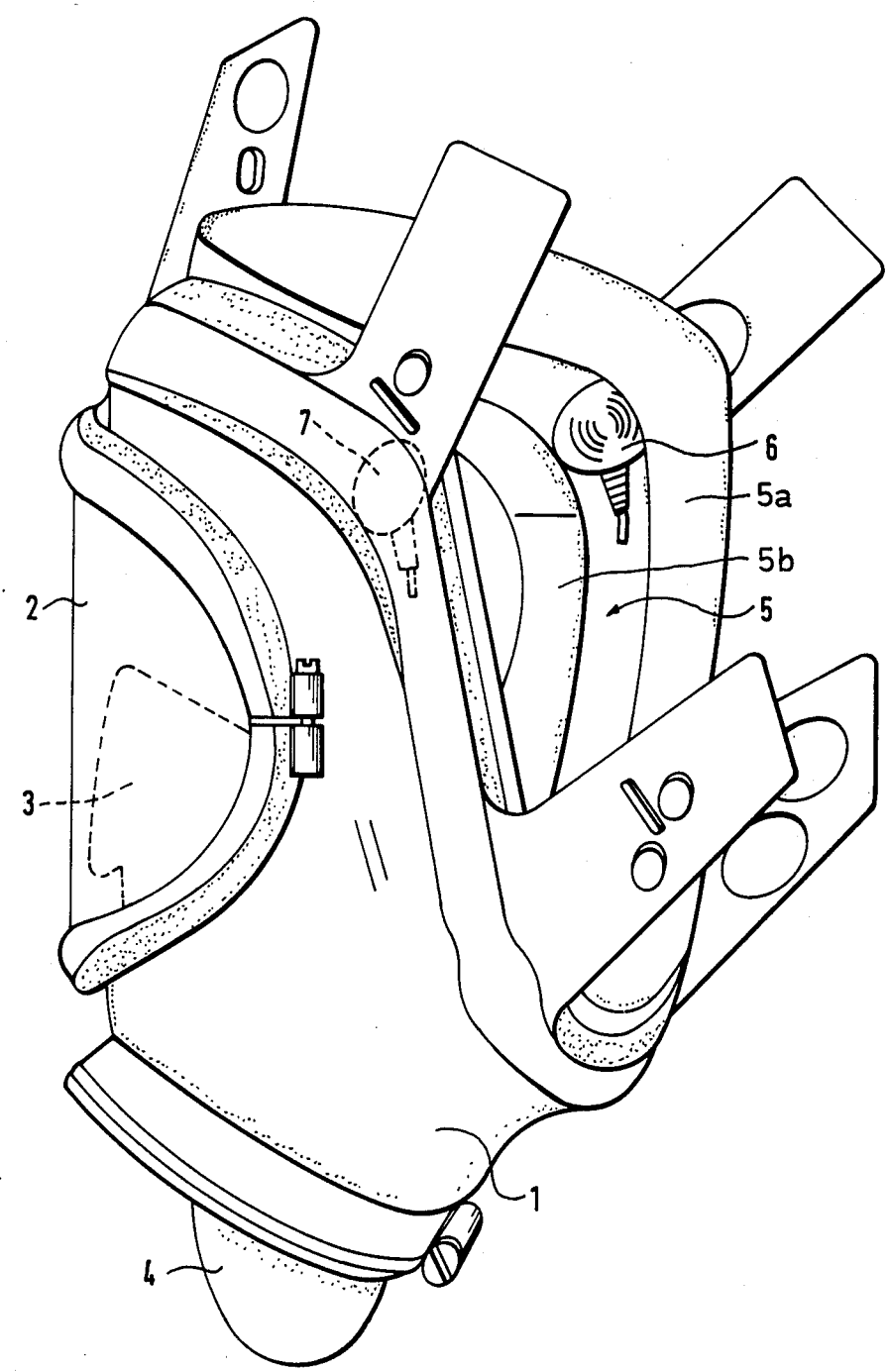

PROTECTIVE MASK HAVING A BUILT-IN SENSOR FOR MONITORING VITAL FUNCTIONS

FIELD OF THE INVENTION

The invention relates to an arrangement for monitoring vital functions having at least one sensor held to the body.

BACKGROUND OF THE INVENTION

An arrangement of the kind described above is disclosed in German published patent application DE-OS 31 06 315. This known arrangement is utilized for monitoring the circulatory system, measuring blood pressure and to permit self-monitoring by persons having circulatory diseases; however, it can also be used by persons who during work or when engaging in sport activity must remain under special supervision of a physician.

The requirement of monitoring vital functions is, however, not limited to the area of medicine; instead, it is also needed for persons who must perform rescue operations with breathing protection equipment such as fire-fighting personnel either in service or during practice sessions as well as rescue or deep sea divers or by workers who belong to a mine disaster rescue team.

Such activities under difficult conditions cause an extreme stress on the performance capability of the human body which is easily overestimated especially when persons have to be rescued under time pressure. In these situations there often is the danger that the limits of endurance is recognized too late during the rescue work and the rescue operation can become endangered in that the particular rescue worker becomes unavailable for the operation without this being monitored or otherwise noticed.

The known arrangement provides that an appropriate sensor be attached to the holders of a spectacle frame for monitoring vital functions. The sensor is pressed against the temple region of the wearer by the clamping pressure and this can be supported as needed by means of a band pulling the holders of the spectacle frame together.

It is a disadvantage of this known arrangement that a spectacle frame must be worn in each instance even when the particular person does not wear spectacles. In addition, such a spectacle frame unnecessarily hinders free movement when wearing a face mask. The required sealing is not assured when full masks are worn.

Furthermore, the contact between the surface of the skin and the sensor can be interrupted because of slippage by the formation of perspiration on the skin of the wearer during strenuous work activity.

SUMMARY OF THE INVENTION

In view of the foregoing, it is an object of the invention to provide an arrangement for monitoring vital functions which is improved especially in that a simple and reliable placement of the sensor is made possible especially when utilizing heavy breathing protection equipment. It is a further object of the invention to provide such an arrangement which causes the sensor to remain in place during difficult conditions of use.

For the attachment of the sensor, it is intended that no ancillary means be required for the purpose of holding the sensor which could possibly be disturbing.

The arrangement according to the invention is for monitoring vital functions and includes a breathing protective mask having an inner surface facing the wearer thereof; and, a sensor for sensing a vital function is mounted on the inner surface of the mask.

The advantages of the invention are essentially seen in that the appropriate sensor automatically lies against the suitable location appropriate for the sensor already when the breathing protective mask is placed in position on the wearer. The breathing-protective mask is preferably a full mask and presses the sensor against the facial region of the wearer under pressure if required. Several sensors can be provided for different functions in accordance with the monitoring desired. The sensors lie against the surface of the face of the wearer in accordance with their purpose and configuration and can also be positioned in the interior space of the breathing-protective mask. Such sensors can, for example, measure the heart rate, breathing rate, respiratory pressures or body temperature.

An especially favorable position for the sensor with respect to making the same non-slippable and also with respect to saving space is the sealing rim of the breathing-protective mask. In order to assure the sealing functions of the full mask, a firm contact engagement of the sealing rim with the periphery of the face is required and the available aids such as mask-holding bands permit the full mask to tightly engage the face even under difficult working conditions. In this way, a tight and non-slip contact engagement of the sensor on the surface of the skin is assured at the same time.

The cavity of a double-bead seal affords an especially advantageous position for the sensor. This provides increased protection of the sensor against outside influences.

Preferably, a sensor in the form of a heart rate detector or a contact thermometer for determining body temperature is provided.

BRIEF DESCRIPTION OF THE DRAWING

The single FIGURE of the drawing is a perspective view of the arrangement according to the invention for monitoring vital functions.

DESCRIPTION OF THE PREFERRED EMBODIMENTS OF THE INVENTION

The mask body includes a viewing window 2 and an inner half-mask 3 which, in turn, includes an exhale valve 4. The mask body 1 is surrounded about the periphery by a sealing rim 5 which accommodates sensor 6 in the temple region of the wearer of the mask. The sensor 6 monitors the heart rate and can, for example, be configured as a pressure-sensitive element which detects the pulse pressure of the temple artery. The sensor 6 supplies a corresponding signal either via a measuring lead (not shown) or via telemetry to an evaluation apparatus which is likewise not shown for indicating the heart rate.

The sealing rim 5 of the mask can include two mutually adjacent sealing beads 5a and 5b which extend around the peripheral region of the mask. The mutually adjacent sealing beads conjointly define a cavity therebetween and the sensor 6 is seated in the cavity so as to be in contact engagement with the wearer of the mask when the mask is worn.

An additional contact thermometer 7 can be mounted on the side of the sealing rim 5 opposite sensor 6 in order to detect the body temperature.

It is understood that the foregoing description is that of the preferred embodiments of the invention and that various changes and modifications may be made thereto without departing from the spirit and scope of the invention as defined in the appended claims.

What is claimed is:

1. Arrangement for monitoring vital functions, the arrangement comprising:
   a breathing protective mask having an inner surface facing a wearer thereof;
   a sensor for sensing a vital function of the wearer when held in contact engagement with the head of the wearer;
   said mask having sealing rim means for defining an uninterrupted seal with the head of the wearer of said mask;
   cavity means disposed completely within said sealing rim means so as to ensure the integrity of said seal; and,
   said cavity means being formed in said sealing rim means and said sensor being held in said cavity means only by said sealing rim means so as to cause said sensor to be in firm contact engagement with the head of the wearer when the mask is worn.

2. The arrangement of claim 1, said sensor being a temperature detector.

3. The arrangement of claim 1, said sensor being a heart rate detector.

4. Arrangement for monitoring vital functions, the arrangement comprising:
   a breathing protective mask having an inner surface facing a wearer thereof;
   a sensor for sensing a vital function of the wearer when held in firm contact engagement with the head of the wearer;
   said mask having a peripheral region at which the mask is placed on the head of the wearer;
   two mutually adjacent sealing beads extending around said peripheral region; said sealing beads defining an uninterrupted seal with the head of the wearer;
   said mutually adjacent sealing beads conjointly defining a cavity therebetween; and,
   said sensor being seated in said cavity so as to be held in place therein by said sealing beads so as to cause said sensor to be in firm contact engagement with the wearer of the mask.

* * * * *